(12) United States Patent
Yang et al.

(10) Patent No.: US 8,410,781 B1
(45) Date of Patent: Apr. 2, 2013

(54) HIGH TEMPERATURE SUPERCONDUCTOR RECEIVER COIL MAGNETIC RESONANCE IMAGING SYSTEMS AND METHODS COMPATIBLE WITH AN INFANT INCUBATOR

(75) Inventors: Edward S. Yang, Shatin (HK); Geng Li, Shatin (CN); Frederick Cheng, Tseung Kwan O (HK)

(73) Assignee: Hong Kong Applied Science and Technology Research Institute Co., Ltd., Hong Kong (CN)

( * ) Notice: Subject to any disclaimer, the term of this patent is extended or adjusted under 35 U.S.C. 154(b) by 493 days.

(21) Appl. No.: 12/825,165

(22) Filed: Jun. 28, 2010

(51) Int. Cl.
  *G01V 3/00* (2006.01)
  *A61B 5/05* (2006.01)
(52) U.S. Cl. .................. 324/318; 600/410; 600/411
(58) Field of Classification Search .......... 324/300–322; 600/407–435; 382/128–132; 424/132.1
  See application file for complete search history.

(56) References Cited

U.S. PATENT DOCUMENTS

| | | | | |
|---|---|---|---|---|
| 5,258,710 A | * | 11/1993 | Black et al. | 324/309 |
| 6,169,399 B1 | * | 1/2001 | Zhang et al. | 324/318 |
| 6,943,550 B2 | | 9/2005 | Cheng et al. | |
| 7,517,834 B2 | | 4/2009 | Wong et al. | |
| 7,859,264 B2 | * | 12/2010 | Wosik et al. | 324/318 |
| 8,106,656 B2 | * | 1/2012 | Wosik et al. | 324/318 |
| 2006/0134099 A1 | * | 6/2006 | Koprowski et al. | 424/132.1 |
| 2008/0278166 A1 | * | 11/2008 | Wosik et al. | 324/318 |
| 2010/0066367 A1 | | 3/2010 | Ma et al. | |
| 2011/0124507 A1 | * | 5/2011 | Wosik et al. | 505/162 |

OTHER PUBLICATIONS

Jean-Christophe Ginefri et al, "High Temperature Superconducting Surface Coil for In Vivo Microimaging of the Human Skin" Magn. Res. in Medicine, 45, 376-382 (2001).

* cited by examiner

*Primary Examiner* — Patrick Assouad
*Assistant Examiner* — Tiffany Fetzner
(74) *Attorney, Agent, or Firm* — Fulbright & Jaworski L.L.P.

(57) ABSTRACT

Systems and methods which employ a high temperature superconductor (HTS) receiver coil configuration for MRI analysis of small volume subjects, such as infants, are shown. Embodiments provide a HTS tape RF phase array receiver coil implementation. The foregoing HTS tape receiver coil implementation may be provided in a Helmholtz coil configuration. With such a Helmholtz coil configuration, circuitry is preferably provided to provide tuning, matching, and/or decoupling with respect to the HTS receiver coils. Embodiments implement a cryostat configuration to maintain one or more HTS receiver coils at a desired operating temperature (e.g., $\leq 77°$ K) while providing a safe environment for a subject (e.g., infant) being imaged.

24 Claims, 8 Drawing Sheets

HIGH TEMPERATURE SUPERCONDUCTOR RECEIVER COIL MAGNETIC RESONANCE IMAGING SYSTEMS AND METHODS COMPATIBLE WITH AN INFANT INCUBATOR

TECHNICAL FIELD

The present invention relates generally to magnetic resonance imaging and, more particularly, to the use of high temperature superconductor receive coils for magnetic resonance imaging.

BACKGROUND OF THE INVENTION

Magnetic resonance imaging (MRI) provides an excellent, non-invasive diagnosis tool for many, often life threatening, diseases. MRI is particularly useful in the study and diagnosis of brain diseases. Accordingly, MRI systems have received wide acceptance by radiologists and other medical professionals for diagnostic use despite the high cost of acquiring and operating such systems.

Tragically, infants, particularly premature infants, may be afflicted with diseases that may affect their future development. For example, infants may suffer from various diseases of the brain, such as hemorrhage, infarction, hypoxia-ischemia, which if improperly diagnosed may cause severe developmental issues and even be life threatening. Accordingly, the use of MRI systems in studying and diagnosing disease in infants in many situations is highly desirable.

Despite the desirability of use of MRI systems in studying and diagnosing disease in infants, such use is not without challenge. For example, there are presently no readily available MRI systems specifically adapted for infant use. The MRI systems that are available for use present issues with respect to limited choice of radio frequency (RF) receiver coils (i.e., available RF receiver coils typically do not include a configuration fully matching the needs of infant use). This results in infant MRI requiring the use of the relatively high field strength (e.g., 1.5 Tesla (T)) MRI systems to provide acceptable image quality for diagnosis. The use of high field MRI systems on infants results in many undesired consequences, such as relatively high scanning costs, increased noise levels experienced by the infant, increased exposure to RF energy by the infant, etc. However, merely reducing the field strength for imaging infants is not possible as the configurations thereof would produce images of unacceptable poor image quality.

In addition to the foregoing, present MRI systems present logistical issues with respect to their use with infants. For example, with present MRI system configurations transportation of a premature infant between the scanning room and the neonatal intensive care unit (NICU) is risky as the premature infant should not be subjected to too excessive movement and various environments.

BRIEF SUMMARY OF THE INVENTION

The present invention is directed to systems and methods which employ a high temperature superconductor (HTS) receiver coil configuration for MRI analysis of small volume subjects, such as infants. Embodiments of the invention provide a HTS tape RF phase array receiver coil implementation. The foregoing HTS tape receiver coil implementation may be provided in a Helmholtz coil configuration. With such a Helmholtz coil configuration, circuitry is preferably provided to provide tuning, matching, and/or decoupling with respect to the HTS receiver coils. Embodiments implement a cryostat configuration to maintain one or more HTS receiver coils at a desired operating temperature (e.g., $\leq 77°$ K) while providing a safe environment for a subject (e.g., infant) being imaged.

Embodiments of the invention are configured for accommodating infants or other subjects requiring special handling. For example, an embodiment of the present invention may dispose HTS receiver coils of a Helmholtz coil configuration on or in an incubator, thereby facilitating MRI analysis of an infant without removal of the infant from the incubator's controlled environment. Additionally or alternatively, embodiments of the invention may adapt HTS receiver coils of a Helmholtz coil configuration to receive an infant, or portion thereof (e.g., head), to facilitate high quality image generation. Accordingly, embodiments of the invention provide MRI systems and methods uniquely suitable for use with respect to infants and which are cheaper and safer to operate by enabling infant MRI with very low-field MRI system (e.g., $\leq 0.5$ T) while providing superior image quality.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

In order to aid in understanding the concepts of the present invention, underlying considerations which led the present inventors to embodiments herein are discussed below. Embodiments of the invention are described following the discussion of these underlying considerations.

A higher signal-to-noise ratio (SNR) is desirable to improve image quality and/or to reduce data acquisition time. The SNR associated with operation of a MRI system for collecting image data may be expressed as follows:

$$\text{SNR } \alpha B_0/\text{sq. root}(R_c T_c + R_s T_s) \tag{1}$$

where Rc is the electrical resistance of the RF receiver coil, Tc is the temperature of the RF receiver coil, Rs is the resistance of the imaging sample, and Ts is the temperature of the imaging sample. Sample noise (RsTs) is Johnson noise which increases with sample temperature (Ts) and the magnetic field strength of the MRI scanner ($B_0$) (e.g., 0.5 T, 1.5 T, 3 T). As can be appreciated from equation (1), the SNR of the MRI system improves with the lower receiver coil resistance (Rc) and lower receiver coil temperature (Tc).

A HTS receiver coil may be operated in a superconducting region, and thus provide negligible resistance (i.e., Rc≈0). For example, a HTS tape RF phase array receiver coil implementation at 77° K becomes superconducting with negligible resistance. Such configurations are utilized according to embodiments to provide improved SNR for MRI system operation.

The theoretical SNR gain achieved through use of a HTS receiver coil configuration over a traditional metal (e.g., copper) receiver coil configuration may be expressed as follows:

$$\frac{SNR(HTS)}{SNR(\text{metal})} = \frac{\sqrt{R_c(\text{metal})T_c(\text{metal}) + R_sT_s}}{\sqrt{R_c(HTS)T_c(HTS) + R_sT_s}} \tag{2}$$

where:

$$Rc = \frac{L\omega_o}{Qu} \tag{3}$$

$$Rs = \frac{L\omega_o o(Q_u - Q_L)}{(Q_u - Q_L)} \tag{4}$$

$$L = \frac{1}{C(\omega_o)^2} \tag{5}$$

and where $Q_U$ is the quality factor of the unloaded coil and $Q_L$ is the quality factor of the loaded coil. Example quality factors for exemplary HTS and metal receiver coils are set forth in the table below.

| Quality Factor | | |
|---|---|---|
| Status | HTS tape (77° K.) | Copper (300° K.) |
| Unloaded ($Q_U$), Earth B-field | 5200 | 130 |
| Unloaded ($Q_U$), magnet isocenter | 1100 | 127 |
| Loaded ($Q_L$) with phantom, magnet isocenter | 934 | 124 |
| Loaded ($Q_L$) with human wrist, magnet isocenter | 850 | 124 |

Figure 1:
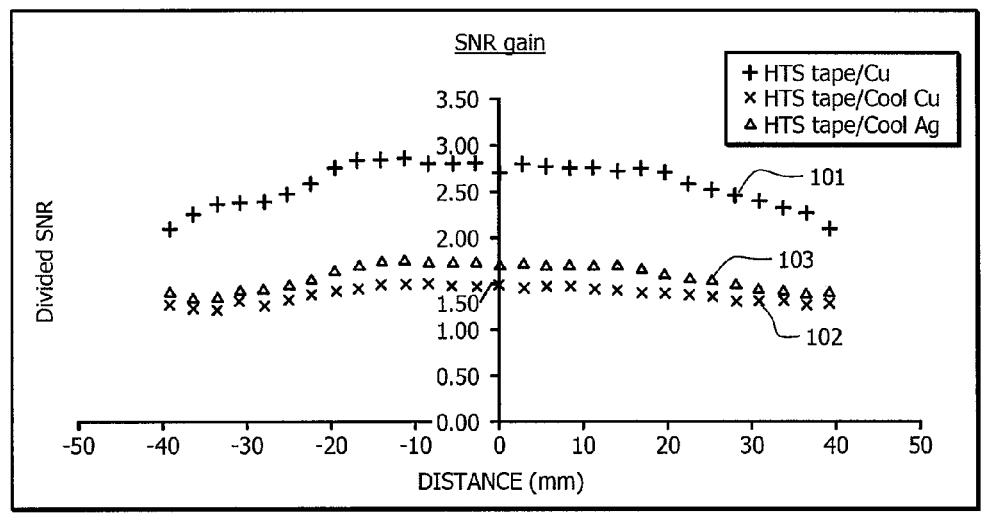
FIG. 1 shows graphical plots of the actual SNR gain achievable by a HTS receiver coil configuration as compared to various metal receiver coil configurations.

FIG. 1 shows graphical plots of the actual SNR gain achievable by a HTS receiver coil configuration as compared to various metal receiver coil configurations at very low MRI field strength (0.2 T) with a phantom. Specifically, the SNR gain of a HTS receiver coil (77° K) configuration verses a typical copper receiver coil (300° K) configuration is shown by plot 101, the SNR gain of a HTS receiver coil (77° K) configuration verses a cool copper receiver coil (77° K) configuration is shown by plot 102, and the SNR gain of a HTS receiver coil (77° K) configuration verses a cool silver coil (77° K) configuration is shown by plot 103. As can be appreciated from the graphical plots of FIG. 1, the SNR gain achievable through use of an HTS receiver coil of embodiments of the invention is ~1.5x-2.7x at 0.2 T.

Figure 2:
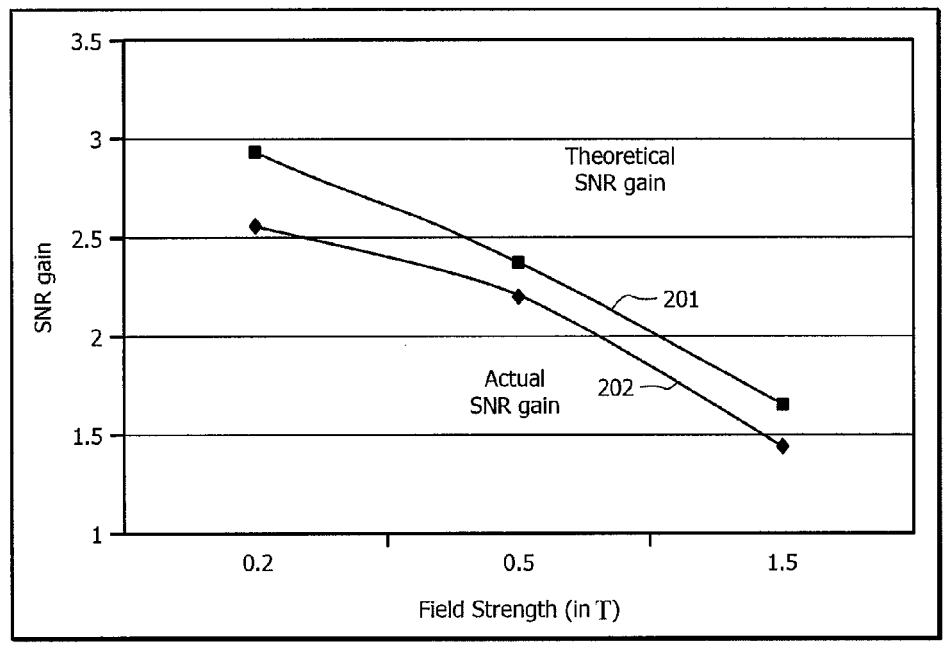
FIG. 2 shows the SNR gain associated with embodiments of a HTS receiver coil is inversely proportional to the field strength.

The foregoing SNR gain achievable through use of a HTS receiver coil is, however, not available in a wide range of field strengths. As shown in FIG. 2, the SNR gain associated with embodiments of a HTS receiver coil is inversely proportional to the field strength. Specifically, both plot 201 of FIG. 2 (theoretical SNR gain) and plot 202 of FIG. 2 (actual SNR gain) show a SNR gain to field strength relationship such that the represented HTS receiver coil is particularly useful due to the SNR gain thereof at field strengths of approximately 0.5 T and below. Accordingly, although traditional MRI systems, implementing metal receiver coils, provide unacceptably poor image quality at very low field strengths (i.e., ≦0.5 T), HTS receiver coil configurations can provide high quality imaging at such field strengths due to their SNR gain.

Figure 3:
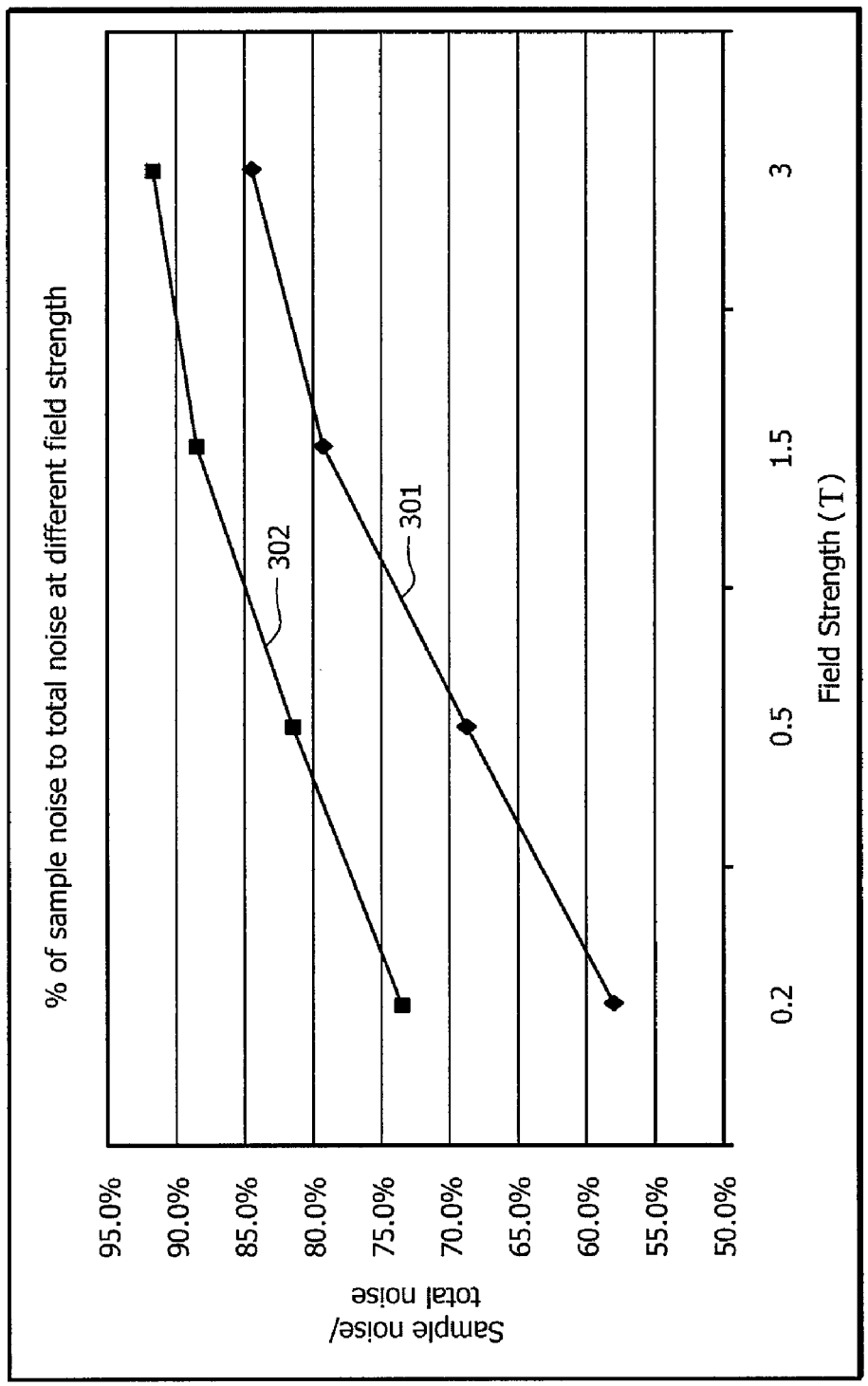
FIG. 3 shows the percentage of sample noise at various field strengths for HTS coil configurations.

As set forth in equation (1) above, the SNR associated with a particular receiver coil configuration has two noise components; one being associated with the coil (RcTc) and the other being associated with the sample (RsTs). Having substantially lowered the noise component associated with the coil in HTS embodiments (i.e., Rc≈0), the noise component associated with the sample becomes dominate with an increase in field strength and/or sample dimension. The percentage of sample noise at various field strengths for a 6-inch HTS coil configuration (plot 301) and for a 12-inch HTS coil configuration (plot 302) is shown in FIG. 3. As can be appreciated from the graph of FIG. 3, HTS coil configurations become sample noise dominate at very low field strengths. Moreover, as can be appreciated from equation (1), increases in the dimension of the sample (e.g., volume, density, etc.) result in increased sample noise. Thus, sample noise dominance of HTS coil configurations results from increased field strength, increased sample dimension, and combinations thereof.

From the foregoing, it can be appreciated that HTS receiver coil configurations of embodiments are particularly useful at very low field strengths (e.g., 0.2 T-0.5 T) with samples of moderate dimension (e.g., ≦16 cm in diameter) or at high field strengths (e.g., 3 T-7 T) with samples of very small dimension (e.g., <1 cm). In contrast, in order to provide a SNR suitable for generating quality images, typical metal receiver coil configurations must at least use field strengths ranging from the lowest of the "low field strengths" (i.e., 1.5

T) to the lowest of the "high field strengths" (i.e. 3 T). Although such a typical metal receiver coil configuration can provide satisfactory imaging, the requisite field strengths and heretofore available configurations are not well suited for use with infants.

Figure 4:
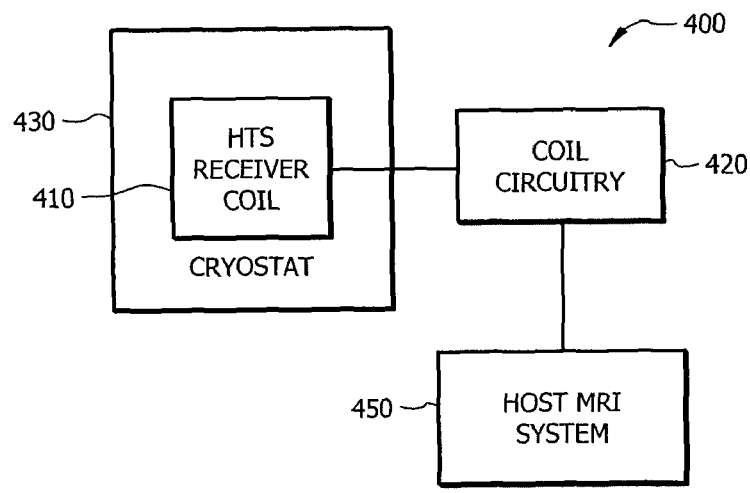
FIG. 4 shows a high level block diagram of a MRI system incorporating a HTS receiver coil configuration of an embodiment of the present invention.

As can be appreciated from the above, embodiments of the present invention thus employ a HTS receiver coil configuration for MRI analysis of small volume subjects, such as infants. FIG. 4 shows a high level block diagram of a MRI system incorporating a HTS receiver coil configuration of an embodiment of the present invention. Specifically, MRI host system 450, such as may comprise a medical diagnostic MRI imaging system well known in the, is shown interfaced to HTS receiver coil subsystem 400 in the illustrated embodiment. HTS receiver coil subsystem 400 is shown to comprise HTS receiver coil 410, coil circuitry 420, and cryostat 420, as will be discussed in further detail below.

HTS receiver coil 410, as will be better appreciated from the discussion below, may comprise one or more receiver coils. Embodiments of the invention provide a HTS tape RF phase array receiver coil implementation. For example, a HTS tape as may be utilized in providing an RF phase array receiver coil of embodiments herein may comprise bismuth strontium calcium copper oxide (BSCCO), perhaps compressed with one or more metals (e.g., silver), formed in a tape. The HTS tape may be shaped to form one or more receiver coils (e.g., one or more 6-inch or 12-inch single loop receiver coils) of HTS receiver coil 410.

Figure 5:
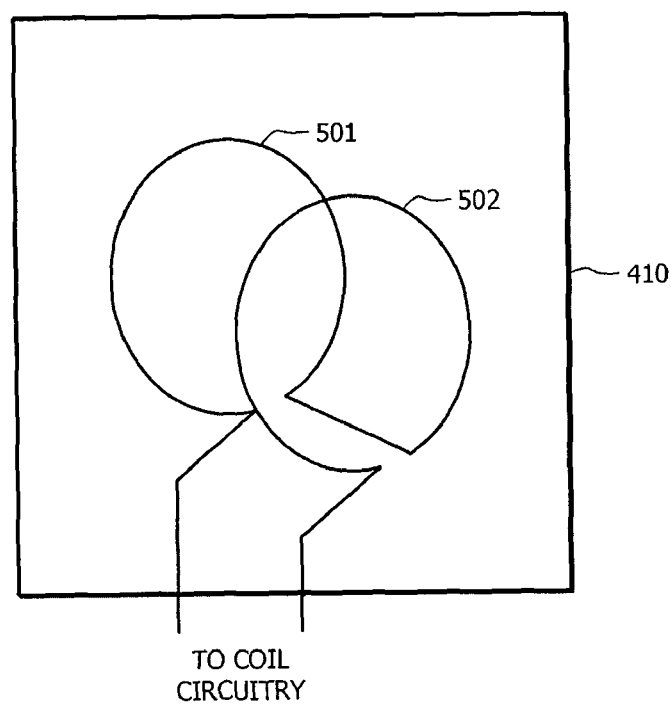
FIG. 5 shows an exemplary Helmholtz coil configuration as may be utilized with respect to HTS receiver coil of embodiments of the invention.

Embodiments of HTS receiver coil 410 implement a multi-coil receiver coil configuration. For example, a preferred embodiment uses a Helmholtz coil configuration, such as may comprise two single loop HTS tape coils disposed in the Helmholtz coil configuration. The use of the Helmholtz coil configuration may enhance the penetration depth, such as to facilitate imaging of an infant's head. The penetration depth (i.e., the effective imaging depth) of the receiver coil in a Helmholtz configuration is approximately the diameter of the coil itself. For effectively decoupling the coils of a Helmholtz coil configuration utilized according to embodiments of the invention, the coil spacing is approximately the coil diameter. An exemplary Helmholtz coil configuration as may be utilized with respect to HTS receiver coil 410 is shown in FIG. 5, wherein HTS receiver coil 410 comprises single turn HTS tape coil 501 and single turn HTS tape coil 502. HTS tape coils 501 and 502 of embodiments are approximately 16 cm in diameter and are spaced approximately 16 cm apart.

Coil circuitry 420 of embodiments provides an interface between HTS receiver coil 410 and host MRI system 450 for passing signals collected by HTS receiver coil 410 to image generation circuitry of host MRI system 450. Moreover, coil circuitry 420 of embodiments provides circuitry for enhancing or optimizing the operation of HTS receiver coil 410. Accordingly, coil circuitry 420 of embodiments includes circuitry providing tuning, matching, and/or decoupling with respect to HTS receiver coil 410.

Figure 6:
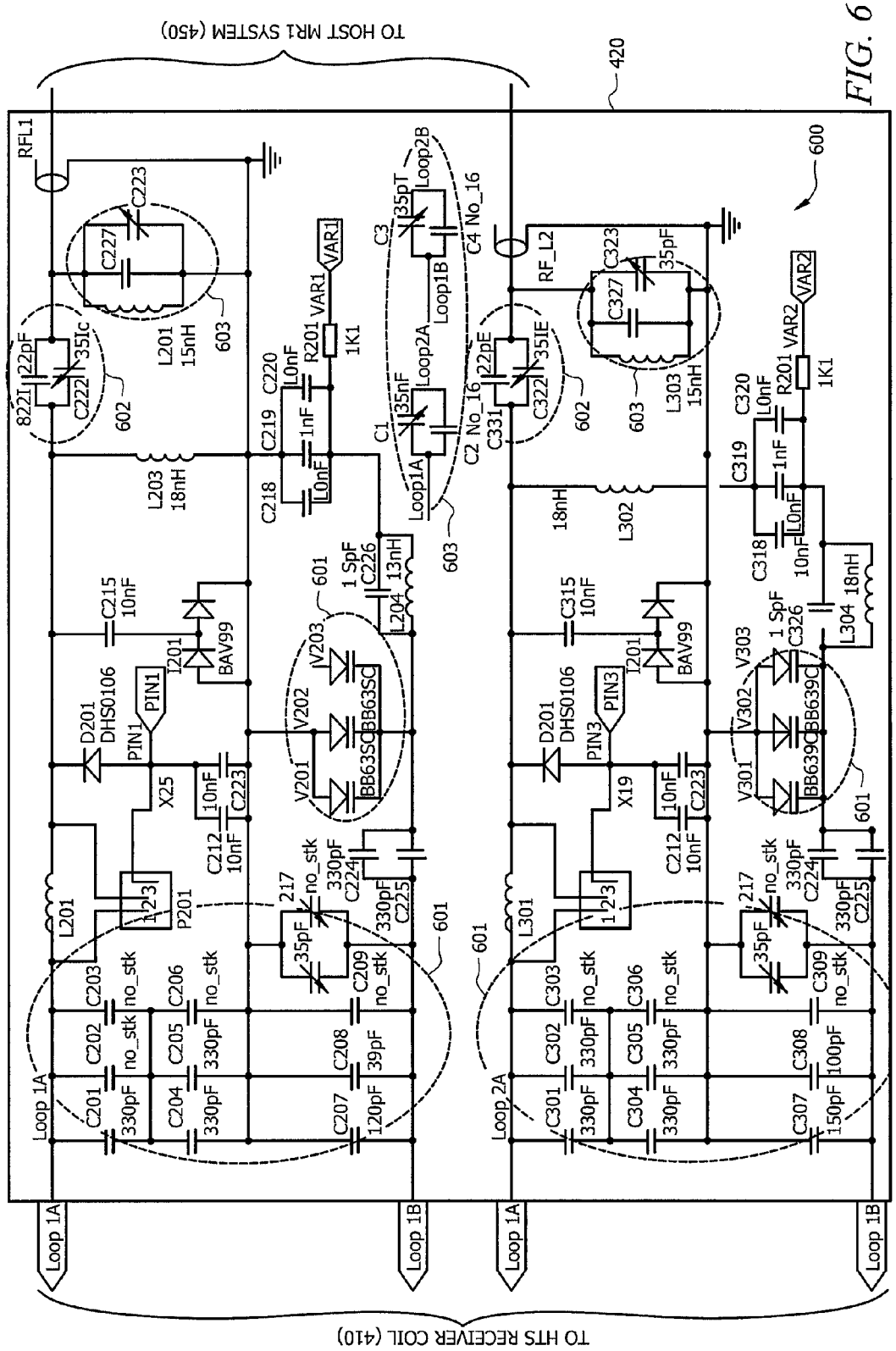
FIG. 6 shows detail with respect to an embodiment of coil circuitry wherein tuning, matching, decoupling circuitry is included.

FIG. 6 shows detail with respect to an embodiment of coil circuitry 420 wherein tuning, matching, decoupling circuitry is included. Specifically, circuitry 600 of FIG. 6 includes tuning circuitry 601, matching circuitry 602, and decoupling circuitry 603.

Tuning circuitry 601 of embodiments provides circuitry which tunes the resonant frequency of HTS receiver coil 410 to match the field frequency of host MRI system 450. Such tuning circuitry preferably includes one or more trimmer (e.g., adjustable capacitors) to facilitate adjustment in the field by an operator for precisely tuning to the field frequency of a host MRI system. It should be appreciated that manufacturing differences, operating temperatures, component age, etc. may affect both the resonance frequency of HTS receiver coil 410 and the field frequency of host MRI system 450. Accordingly, tuning circuitry 601 of embodiments facilitates tuning (e.g., periodically, prior to each use, etc.) for enhanced or optimized operation of HTS receiver coil subsystem 400 with host MRI system 450.

Matching circuitry 602 of embodiments provides circuitry which matches the output impedance of circuitry 600 to the input impedance of host MRI system 450. Through proper matching provided by matching circuitry of embodiments, a high SNR provided by the HTS receiver coil configuration may be maintained as the signal is provided to the host MRI system for image generation. Accordingly, such matching circuitry preferably includes one or more trimmer (e.g., adjustable capacitors) to facilitate adjustment in the field by an operator for precisely matching to the impedance of a host MRI system for enhanced or optimized operation of HTS receiver coil subsystem 400 with host MRI system 450.

Decoupling circuitry 603 of embodiments provides circuitry which decouples the coils of a multi-coil HTS receiver coil implementation. In a multi-coil configuration, the coils will typically interact with each other providing undesirable results. Thus, decoupling circuitry of embodiments provides decoupling such that coils of the HTS receiver coil will not substantially interact with each other. Such decoupling circuitry preferably includes one or more trimmer (e.g., adjustable capacitors) to facilitate adjustment in the field by an operator for decoupling coils of HTS receiver coil 410 for enhanced or optimized operation of HTS receiver coil subsystem 400.

It should be appreciated that circuitry 600 of embodiments provides non-superconductor signal paths coupled to the superconductor signal paths of HTS receiver coil 410. Accordingly, the connections between these two types of signal paths are preferably adapted to minimize the electrical resistance. Accordingly, embodiments of the invention may utilize soldering flux for proper cleaning of soldering joints and soldering compounds such as indium paste in providing connectivity between signal paths of circuitry 600 and signal paths of HTS receiver coil 410.

Figure 7:
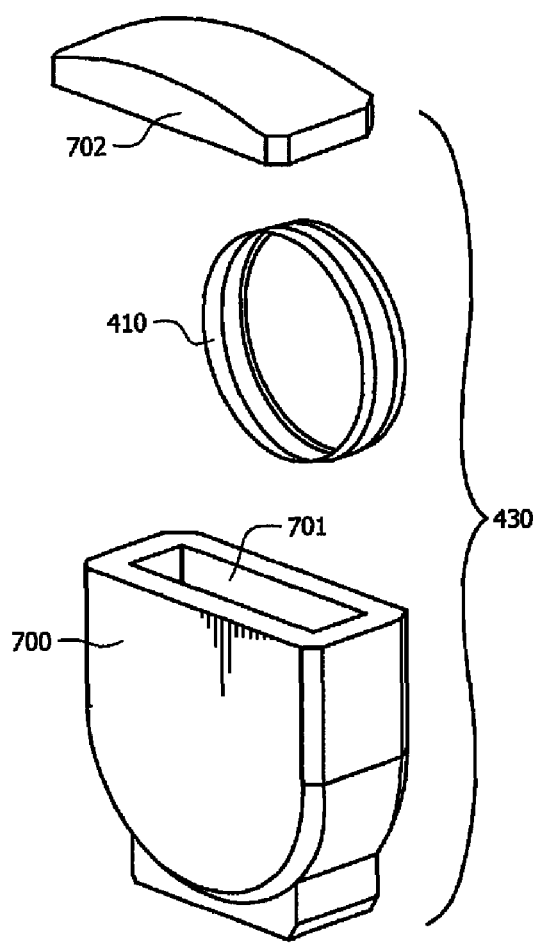
FIG. 7 shows an embodiment of a cryostat as may be utilized according to the present invention.

Cryostat 430 of embodiments is adapted to maintain one or more coil of HTS receiver coil 410 at a desired operating temperature (e.g., $\leq 77°$ K) while providing a safe environment for a subject (e.g., infant) being imaged by the MRI imaging system. Such cryostat preferably includes a housing (e.g., housing 700 of FIG. 7) forming a chamber (e.g., chamber 701 of FIG. 7) in which a HTS receiver coil of embodiments is held at a desired operating temperature. The cryostat housing further preferably provides a high degree of thermal isolation between the aforementioned chamber and a subject being imaged. Such thermal isolation may be provided by the material of the cryostat housing (e.g., forming the chamber walls provided by the cryostat), by insulating material used in addition to the material of the cryostat housing (e.g., disposed within or on chamber walls provided by the cryostat), by the configuration of the cryostat housing (e.g., forming a vacuum chamber within chamber walls provided by the cryostat), or combinations thereof.

It should be appreciated that there are three processes that cause heat transfer: conduction, convection and radiation. In a cryogenic system such as that of cryostat 430, typically no convection is involved and conduction dominates among the three. Therefore, to increase the thermal insulation materials with lower thermal conductivity should be used, whether as the material of the cryostat housing or as insulating material utilized therewith.

Embodiments of the present invention utilize a cold media, such as liquid nitrogen ($LN_2$), to maintain HTS receiver coil 410 at a desired operating temperature (e.g., 77° K). Embodiments herein consider three types of cryostat housing and/or insulating materials for shielding such code media in the cryostat: silica aerogel, Styrofoam and zirconia ceramic. It should be appreciated that each of the foregoing materials is non-magnetic and thus is well suited for use with HTS receiver coil subsystem 400 and MRI host system 450 (e.g., the material will not interfere with the magnetic field of the HTS receiver coil). Compared to the usual materials (i.e., fiberglass, glass, glass composite or their combination), the foregoing materials of embodiments herein offer better thermal insulation, lighter weight, and possibly lower cost.

Silica aerogel keeps the current record for the lowest thermal conductivity in all solid state materials, and it is extremely light. The excellent insulation ability of silica aerogel may allow its use without providing additional insulating configurations, such as high vacuum in the cryostat chamber walls, thus reducing the manufacturing and maintenance costs. Silica aerogel sheets mixed with reinforcing fibers for improved mechanical properties are available for use in embodiments of cryostat 430. Additionally or alternatively, silica aerogel beads, which are readily integrated into structures with various shapes, may be utilized in embodiments of cryostat 430.

Styrofoam has higher thermal conductivity and larger mass than silica aerogel, yet it is still significantly better and lighter than glass. Moreover, Styrofoam is widely available at a low price and can be manufactured into any customized shapes. Accordingly, embodiments of cryostat 430 utilize Styrofoam within or as chamber walls thereof to provide desired thermal isolation.

Zirconia ceramic has the highest thermal conductivity among the foregoing three materials. Nevertheless, zirconia is comparable with glass, if not better. Zirconia is widely used in spacecraft and automobile industry as top layers of a multilayer insulation structure due to its mechanical protective properties. Although it is heavier than silica aerogel and Styrofoam, zirconia offers better mechanic properties. Accordingly, embodiments of cryostat 430 utilize zirconia for providing desired thermal isolation. For example, embodiments may employ zirconia as a surface layer of cryostat 430, perhaps disposed over another insulating material such as silica aerogel and/or Styrofoam.

To block the radiation which can cause heat transfer, other than conduction, from the ambient environment to the cryostat chamber, a thin metal coating such as silver may be used on one or more surface of the cryostat. For example, chamber 701 and a corresponding bottom surface of top 702 may be lined with thin metal for radiation shielding. Additionally or alternatively, exterior surfaces of cryostat 430 may be lined with thin metal for radiation shielding. It should be appreciated that such radiation shielding utilized according to embodiments of the invention should be non-magnetic to avoid interfering with HTS receiver coil subsystem 400 and MRI host system 450 (e.g., the material will not interfere with the magnetic field of the HTS receiver coil).

Figure 8A:
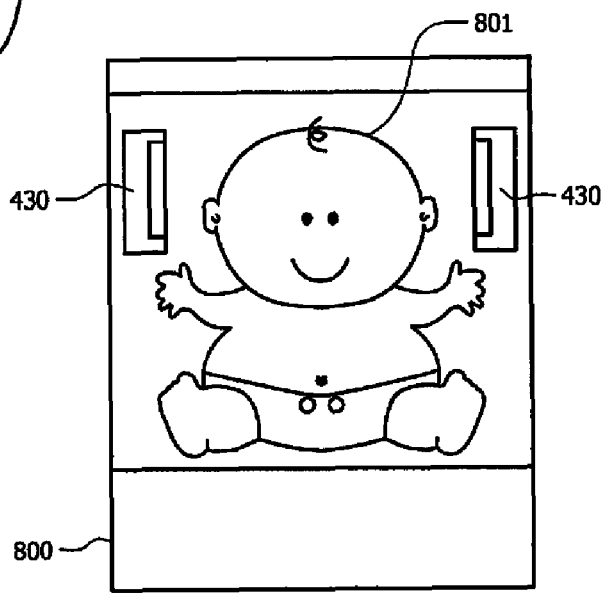
FIGS. 8A and 8B show an embodiment wherein cryostats, containing one or more HTS coils, are disposed in an incubator.
Figure 8B:
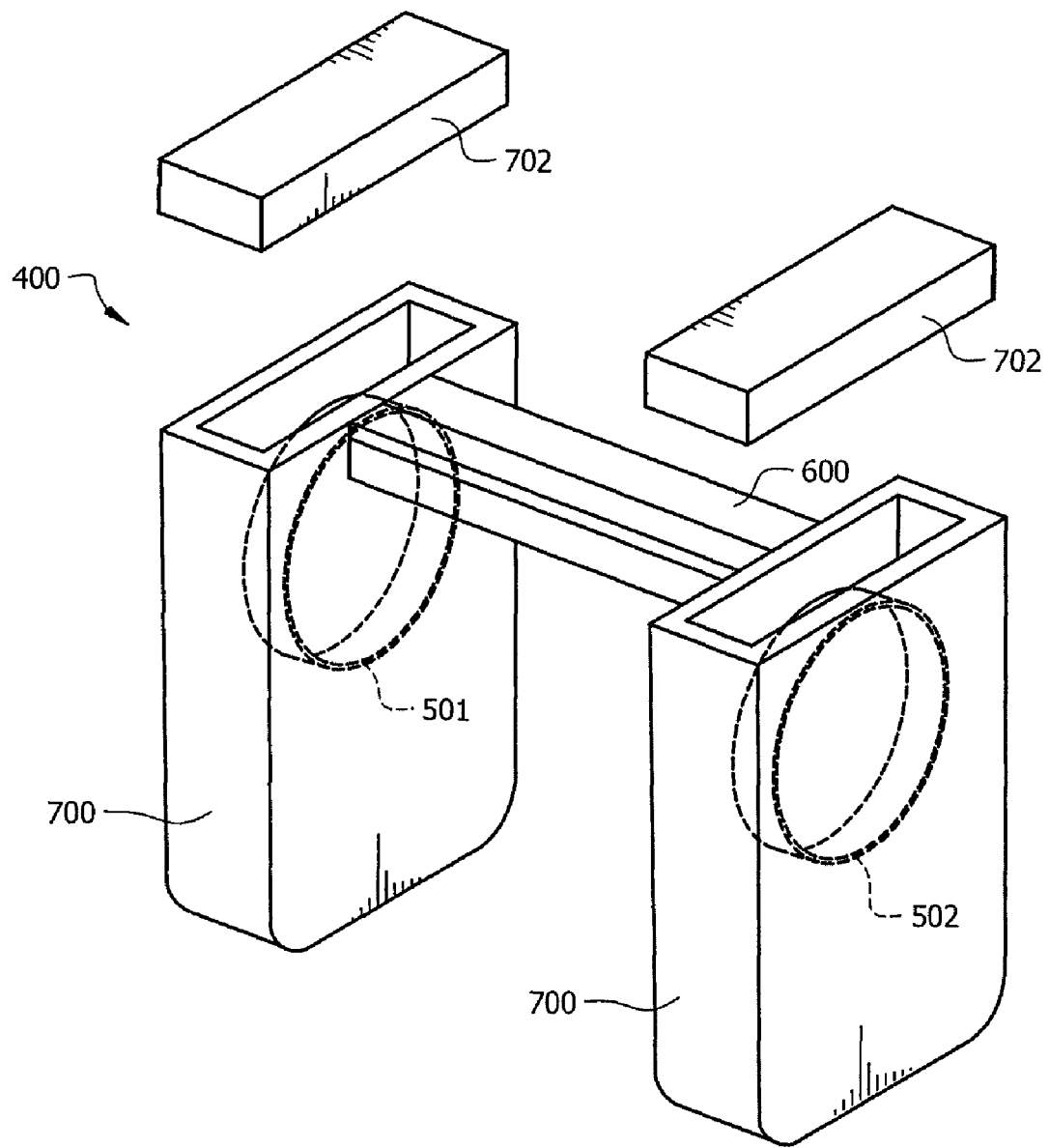

Embodiments of HTS receiver coil subsystem 400 are configured for accommodating infants or other subjects requiring special handling. For example, an embodiment of the present invention may dispose HTS receiver coils on or in an incubator, thereby facilitating MRI analysis of an infant without removal of the infant from the incubator's controlled environment. FIG. 8A shows one such embodiment wherein cryostats 430, containing HTS coils of HTS receiver coil 410, are disposed in incubator 800. Specifically, as shown in more detail in FIG. 8B cryostat housings 700 containing single turn HTS tape coils 501 and 502 of HTS receiver coil 410 may be coupled by circuitry 600 in a configuration adapted for disposing in incubator 800.

Incubator 800 provides a safe, controlled environment in which subject 801 (e.g., a premature infant) is maintained. Incubator 800, and thus HTS receiver coil subsystem 400, may be placed on or within a scanning head of MRI host system 450 for MRI imaging of subject 801 without the need to remove subject 801 from the incubator environment and with reduced field strength and noise from operation of MRI host system 450.

Figure 9A:
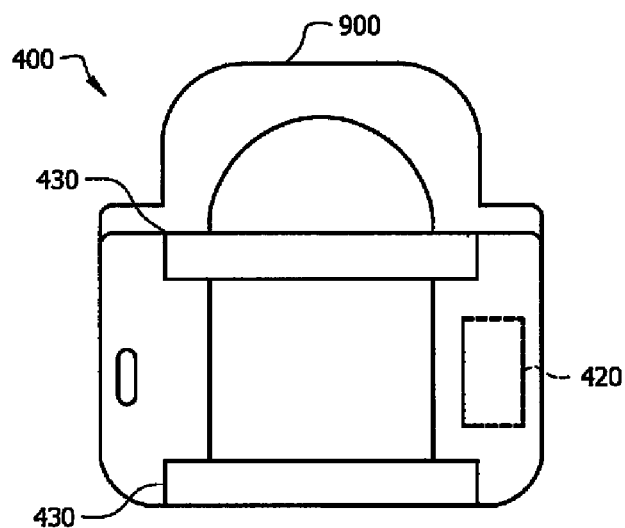
FIGS. 9A and 9B show an embodiment wherein cryostats, containing one or more HTS coils, are disposed with a base shaped to receive a portion of a subject and sized to be disposed in an incubator.
Figure 9B:
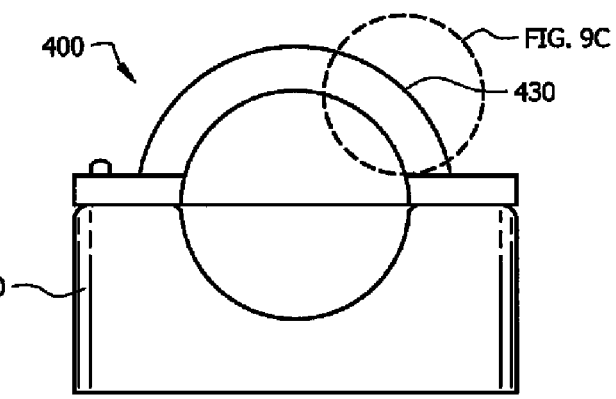

Additionally or alternatively, embodiments of HTS receiver coil subsystem 400 may adapt HTS receiver coils to receive an infant, or portion thereof (e.g., head), to facilitate high quality image generation. For example, an embodiment of the present invention may provide a HTS receiver subsystem shaped to accept a portion of a subject to be imaged and sized to fit within a small environment such as within an incubator. FIGS. 9A and 9B show one such embodiment wherein cryostats 430, containing HTS coils of HTS receiver coil 410, are disposed with base 900 shaped to receive an infant's head and sized to be disposed in an incubator, such as incubator 800 of FIG. 8A. It should be appreciated that the cryostats, and thus the coils, as disposed by base 900 of the embodiment of HTS receiver coil subsystem 400 illustrated in FIGS. 9A and 9B provides open space there between for ventilation and comfort of the subject. Moreover, base 900 of the illustrated embodiment provides a housing for circuitry 600.

Figure 9C:
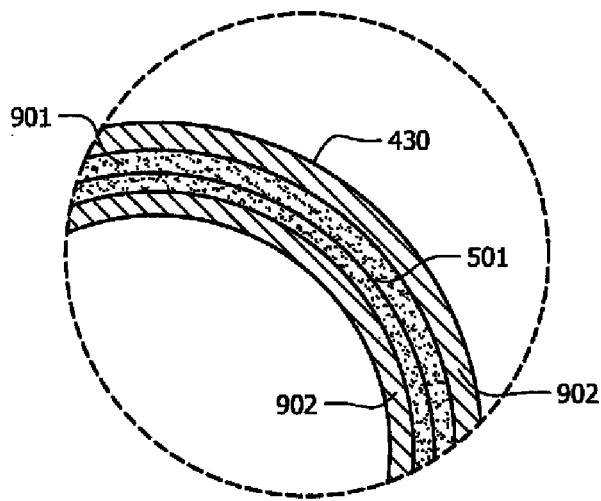
FIG. 9C shows detail with respect to the cryostats of FIGS. 9A and 9B.

As can be seen in FIG. 9C, cryostats 430 provide a chamber in which cold media 901 is held for maintaining HTS receiver coil 410 (e.g., single turn HTS tape coil 501) at a desired temperature. Further as can be seen in FIG. 9C, cryostats 430 are configured to provide thermal isolation using vacuum chamber 902 within chamber walls provided by the cryostat.

In operation, an incubator in which HTS receiver coil subsystem 400 of the embodiment of FIGS. 9A-9C is disposed, may be placed on or within a scanning head of MRI host system 450 for MRI imaging of a subject without the need to remove the subject from the incubator environment and with reduced field strength and noise from operation of MRI host system 450. Accordingly, like the embodiment of FIGS. 8A and 8B, the embodiment of FIGS. 9A-9C provide MRI systems and methods uniquely suitable for use with respect to infants and which are cheaper and safer to operate while providing superior image quality.

Figure 10:
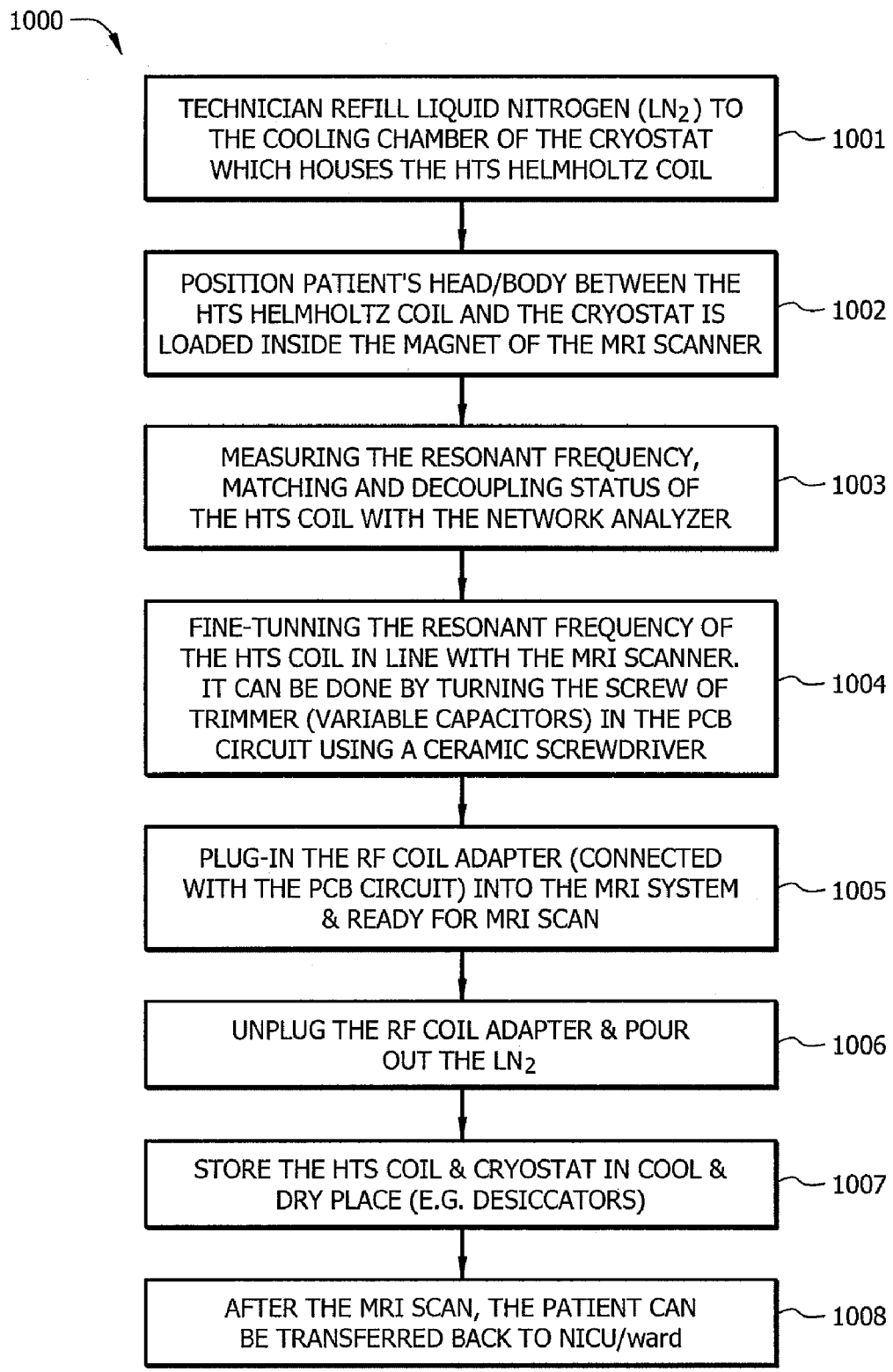
FIG. 10 shows a flow diagram of operation to provide MRI image generation using a HTS receiver coil subsystem in cooperation with a MRI host system according to embodiments of the invention.

Having described various embodiments of the present invention, a description of operation to provide MRI image generation using HTS receiver coil subsystem 400 in cooperation with MRI host system 450 according to embodiments is provided with reference to flow diagram 1000 of FIG. 10. At block 1001 of the illustrated embodiment, a technician fills a chamber of cryostat 430 with cold media (e.g., $LN_2$) to cool one or more HTS coils of HTS receiver coil 410. At block 1002, a portion of the subject to be imaged (e.g., infant's head) is disposed in the proper position with respect to HTS receiver coil 410. For example, HTS receiver coil 410 and cryostat 430 may be disposed within or on an incubator, and thus the subject (e.g., infant) may be disposed within the incubator in a proper relationship to HTS receiver coil 410. Thereafter, cryostat 430 (and thus HTS receiver coil 410, the subject, and possibly an incubator or other structure incarcerating the foregoing) is loaded into the magnet of MRI host system 450.

At block 1003 a technician operates the magnet of MRI host system 450 and measures the resonant frequency, matching, and decoupling status of HTS receiver coil subsystem 400. For example, the technician may use a network analyzer to measure the resonant frequency, matching, and decoupling status of the HTS receiver coil subsystem 400 while the magnet of MRI host system 450 is energized. In operation according to embodiments of the invention, the connections of coil circuitry 420 which are to be connected to MRI host system 450 in imaging operation, are connected to the aforementioned network analyzer for the aforementioned measurements.

At block 1004 of the illustrated embodiment, a technician performs fine-tuning of HTS receiver coil subsystem 400. For example, where HTS receiver coil 410 was found to be out of tune with the resonant frequency of MRI host system 450, the technician may adjust the resonant frequency of HTS receiver coil 410 by adjusting a trimmer (e.g., variable capacitors) of coil circuitry 420. Such adjustment is preferably made using non-magnetic tools, such as a ceramic screwdriver, to facilitate fine-tuning while the magnet of MRI host system 450 remains energized.

After HTS receiver coil subsystem 400 is satisfactorily fine-tuned for tuning, matching, and/or decoupling, operation according to the illustrated embodiment is ready for MRI imaging. Accordingly, the connections of coil circuitry 420 which are adapted for connection to MRI host system 450 are connected to MRI host system 450 for MRI scanning and image generation, as shown at block 1005. MRI host system 450 is thereafter operated to provide desired MRI scanning and image generation. It should be appreciate that operation of MRI host system 450 with HTS receiver coil subsystem 400 allows for low field operation (e.g., $\leq 0.5$ T) for imaging subjects such as infants while providing desired image quality.

At block 1006, after MRI scanning is complete, HTS receiver coil subsystem 400 is disconnected from MRI host system 450. The cold media contained by cryostat 430 may be removed as HTS receiver coil 410 is no longer operational, at least for this scanning session, and thus need not be maintained at a particular temperature. Correspondingly, at block 1007, HTS receiver coil 410 and cryostat 420 may be stored in a cool, dry place (e.g., desiccators) for later reuse.

At block 1008 of the illustrated embodiment, the subject is released from the MRI operations. For example, the subject (e.g., infant) may be transferred back to a NICU for continued monitoring and treatment. It should be appreciated that the subject may be transported to the MRI scanning session in an incubator, retained in the incubator during the MRI scanning session, and transported from the MRI scanning session in the incubator according to embodiments of the invention.

As can be appreciated from the foregoing, embodiments herein provide a HTS tape Helmholtz RF receiver coil and cryostat with built-in tuning, matching, and decoupling circuit optimized for enhancing the SNR of infant MR imaging at low field strengths. The HTS receiver coil may implemented as a standalone coil, or it may be operatively coupled to other structure, such as an MRI incubator. Moreover, although embodiments have been described herein with respect to multi-coil implementations, it should be appreciated that concepts of the present invention may be applied to alternative embodiments implementing other coil configurations (e.g., a single HTS coil configuration, a HTS micro coil array, etc.). Likewise, although embodiments have been described herein with respect to signal turn coils, the concepts of the present invention may be applied to alternative embodiments implementing multiple turn coil configurations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system comprising:
    a high temperature superconductor (HTS) receiver coil, wherein the HTS receiver coil comprises a multi-coil Helmholtz coil configuration, wherein the HTS receiver coils of the multi-coil Helmholtz coil configuration are adapted for very low field strength imaging of a small volume subject;
    a cryostat adapted to incarcerate the HTS receiver coil in a cold media and to maintain the HTS receiver coil at a desired operating temperature during magnetic resonance imaging (MRI) of a subject, wherein the cryostat and HTS receiver coils are adapted for disposing in an infant incubator; and
    coil circuitry coupled to the HTS receiver coil and adapted to interface the HTS receiver coil to a MRI host system, wherein the coil circuitry comprises adjustable tuning circuitry adapted to tune a resonant frequency of the HTS receiver coil to a field frequency of the MRI host system.

2. The system of claim 1, wherein the coil circuitry further comprises adjustable matching circuitry adapted to match an output impedance of the coil circuitry to an input impedance of the MRI host system.

3. The system of claim 1, wherein the HTS receiver coil comprises a single turn coil.

4. The system of claim 1, wherein each HTS receiver coil of the multi-coil Helmholtz coil configuration comprises a single turn coil.

5. The system of claim 1, wherein the coil circuitry further comprises adjustable decoupling circuitry adapted to decouple individual HTS receiver coils of the multi-coil Helmholtz coil configuration.

6. The system of claim 1, wherein the HTS receiver coils of the multi-coil Helmholtz coil configuration are operable to provide signal-to-noise gain within the range of 1.5 to 2.7 over corresponding metal receiver coils at the very low field strength.

7. The system of claim 1, wherein the very low field strength is less than or equal to 0.5 Tesla.

8. The system of claim 1, wherein the very low field strength is less than or equal to 0.2 Tesla.

9. The system of claim 1, wherein the cryostat and HTS receiver coils are provided in a free standing configuration adapted to be placed within the infant incubator.

10. The system of claim 1, wherein the cryostat and HTS receiver coils are provided in a configuration adapted to be attached to one or more surface of the infant incubator.

11. A system comprising:
a high temperature superconductor (HTS) receiver coil, wherein the HTS receiver coil comprises a multi-coil Helmholtz coil configuration, wherein the coils of the HTS receiver coil are adapted for low field strength imaging of a small volume subject;
a cryostat adapted to incarcerate each coil of the HTS receiver coil in a cold media and to maintain the coils at a desired operating temperature during magnetic resonance imaging (MRI) of a subject, wherein the cryostat and HTS receiver coil are adapted for disposing in an infant incubator; and
coil circuitry coupled to coils of the HTS receiver coil and adapted to interface the HTS receiver coil to a MRI host system, wherein the coil circuitry comprises decoupling circuitry adapted to decouple the coils of the HTS receiver coil.

12. The system of claim 11, wherein the decoupling circuitry is field adjustable.

13. The system of claim 11, wherein the coil circuitry further comprises adjustable tuning circuitry adapted to tune a resonant frequency of the HTS receiver coil to a field frequency of the MRI host system.

14. The system of claim 11, wherein the coil circuitry further comprises adjustable matching circuitry adapted to match an output impedance of the coil circuitry to an input impedance of the MRI host system.

15. The system of claim 11, wherein each coil of the HTS receiver coil comprise a single turn coil.

16. A method comprising:
disposing a plurality of high temperature super conductor (HTS) receiver coils within an infant incubator into which a subject is to be placed for operating a magnetic resonance imaging (MRI) host system;
disposing the subject in a position relative to the plurality of HTS receiver coils to facilitate MRI of the subject using the HTS receiver coils, wherein the HTS receiver coils are coupled to coil circuitry adapted to provide an interface between the HTS receiver coils and a MRI host system, and wherein the subject comprises an infant;
placing the HTS receiver coils and subject in the magnetic field of a MRI host system; and
operating the MRI host system at a very low field strength and receive signals from the HTS receiver coils through the coil circuitry for generating an image of at least a portion of the subject.

17. The method of claim 16, further comprising:
adjusting at least one of a resonant frequency of the HTS receiver coils to tune to a magnetic field frequency of the MRI host system, an output impedance of the coil circuitry to match an input impedance of the MRI host system, and a decoupler providing decoupling of the HTS receiver coils.

18. The method of claim 17, wherein the adjusting is performed prior to operating the MRI host system for generating the image.

19. The method of claim 18, wherein the adjusting is performed after the placing the HTS receiver coils and subject in the magnetic field of the MRI host system.

20. The method of claim 16, wherein the very low field strength is less than or equal to 0.5 Tesla.

21. The method of claim 16, wherein the very low field strength is less than or equal to 0.2 Tesla.

22. The method of claim 16, further comprising:
introducing a cold media to one or more cryostat which incarcerates the HTS receiver coils to cool the HTS receiver coils to a desired temperature for the operating the MRI host system.

23. A method comprising:
attaching a plurality of high temperature superconductor (HTS) receiver coils indirectly to a surface of an infant incubator into which a subject is to be placed for operating a magnetic resonance imaging (MRI) host system;
disposing the subject in a position relative to the HTS receiver coils to facilitate MRI of the subject using the HTS receiver coils, wherein the HTS receiver coils are coupled to coil circuitry adapted to provide an interface between the HTS receiver coils and a MRI host system, wherein the subject comprises an infant;
placing the HTS receiver coils and subject in the magnetic field of the MRI host system; and
operating the MRI host system at a very low field strength and receive signals from the HTS receiver coils through the coil circuitry for generating an image of at least a portion of the subject.

24. The method of claim 23, wherein the indirectly attaching comprises attaching one or more cryostat which incarcerates the HTS receiver coils to the surface of the infant incubator.

* * * * *

UNITED STATES PATENT AND TRADEMARK OFFICE
CERTIFICATE OF CORRECTION

PATENT NO. : 8,410,781 B1
APPLICATION NO. : 12/825165
DATED : April 2, 2013
INVENTOR(S) : Edward S. Yang et al.

It is certified that error appears in the above-identified patent and that said Letters Patent is hereby corrected as shown below:

In the Specification:

Column 3, Line 37, delete the portion of text reading "(i.e., $Re \approx 0$)" and replace with --(i.e., $Rc \approx 0$)--.

Signed and Sealed this
Twenty-first Day of May, 2013

Teresa Stanek Rea
*Acting Director of the United States Patent and Trademark Office*